United States Patent
Kühn

[11] Patent Number: 5,759,368
[45] Date of Patent: Jun. 2, 1998

[54] ELECTROCHEMICAL GAS SENSOR

[75] Inventor: Uwe Kühn, Wesenberg, Germany

[73] Assignee: Drägerwerk Aktiengesellschaft, Lübeck, Germany

[21] Appl. No.: 786,798

[22] Filed: Jan. 21, 1997

[30] Foreign Application Priority Data

May 11, 1996 [DE] Germany .................. 196 19 169.6

[51] Int. Cl.⁶ .................................................. G01N 27/26
[52] U.S. Cl. ..................... 204/431; 204/403; 205/787; 205/792; 205/794.5
[58] Field of Search ................................ 204/403, 415, 204/431, 432

[56] References Cited

U.S. PATENT DOCUMENTS

| | | | |
|---|---|---|---|
| 3,824,166 | 7/1974 | Deibert | 204/432 |
| 3,998,717 | 12/1976 | Watson et al. | 204/415 |
| 4,401,547 | 8/1983 | Schinkmann et al. | 204/415 |
| 4,406,770 | 9/1983 | Chan et al. | 204/431 |
| 4,436,812 | 3/1984 | Endoh et al. | 204/403 |
| 4,487,055 | 12/1984 | Wolf . | |
| 4,770,026 | 9/1988 | Wolf . | |
| 5,183,550 | 2/1993 | Mattiessen | 204/415 |

FOREIGN PATENT DOCUMENTS 39 04 994 A1  8/1990  Germany .

OTHER PUBLICATIONS

H. Huck, 1974 month unavailable, An Analytical Fuel Cell as an Alcohol Sensor, Z. Anal. Chem., 270, 266–273.

*Primary Examiner*—T. Tung
*Attorney, Agent, or Firm*—McGlew and Tuttle

[57] ABSTRACT

An electrochemical gas sensor with at least two electrodes, with an electrode holder and with an electrolyte in a housing made of an electrolyte-impermeable material is improved in terms of its ease of handling and durability, without compromising the quality of the measurement. The otherwise closed housing has only one inlet capillary and outlet capillary each for the gas to be measured. A heater is provided which forms a gap with the working electrode arranged above the inlet and outlet capillaries. The heater is arranged in the housing in the flow path between the inlet and outlet capillaries. The gas sensor may be designed in the form of a miniaturized, chip-like component.

17 Claims, 2 Drawing Sheets

ELECTROCHEMICAL GAS SENSOR

FIELD OF THE INVENTION

The present invention pertains to an electrochemical gas sensor with at least two electrodes, with an electrode holder and with an electrolyte in a housing made of an electrolyte-impermeable material.

BACKGROUND OF THE INVENTION

Such electrochemical gas sensors have been known for a long time, and they appear from, e.g., the journal Z. Anal Chem., 270, 266–273 (1974), H. Huck. An Analytical Fuel Cell as an Alcohol Sensor, in which a measuring setup that is suitable, in principle, for such investigations is described.

Two platinum/gold electrodes, which are arranged symmetrically in relation to a PVC matrix containing an acid electrolyte and are accommodated in a housing of a suitable design for the entry of gas to be measured, are used.

Depending on the specific design and dimensioning as well as the material selected, the concentrations of certain gas components in samples of the gas to be measured can be determined quantitatively on the basis of the electrochemical reactions taking place.

Various measuring setups and evaluation methods were developed over time especially for the determination of the alcohol content (ethanol) in the air expired by humans, which is explained by the significance of this important field of application for electrochemical gas sensors. The type and quality of the sampling of a gas sample to be measured plays an important role for the determination of concentrations of gas components in the air in volume flows, e.g., in the air expired by humans, which concentrations are subject to variations in time and space, if reliable measurement results are to be obtained.

Various suggestions were correspondingly made for improving the sampling and the design of the measuring setup in order to obtain the most accurate measurement results possible.

Thus, the design of a breath alcohol-measuring device with a mobile diaphragm, by which the breathing gas sample is to be pumped in the direction of the electrochemical analytical fuel cell, is described in U.S. Pat. No. 44,87,055.

U.S. Pat. No. 47,70,026 discloses a device and an evaluation process for detecting the electrons released by the oxidation of the alcohol at one of the electrodes in a breathing gas sample by means of an analytical fuel cell and thus for ultimately determining the concentration of alcohol in the breathing gas sample.

Finally, DE 39 04 994 A1 discloses a device for delivering a gas sample into the measuring chamber of a measuring sensor, i.e., a possibility of improving the sampling of the gas to be measured. One drawback of such a device is that the corresponding electrode may be partially overloaded due to the fact that the entire sample gas flow directly reaches the measurement-sensitive surface of the measuring sensor.

In addition, it would be desirable to have an electrochemical gas sensor of a miniaturized size in order to arrange it as a chip-like component directly on a corresponding evaluation board, so that it would be possible to considerably reduce the size of the entire measuring setup. Furthermore, it would be desirable to improve the heating action of the heating elements used to date, which are to lead to an acceleration of the measurement by the accelerated relevant chemical reaction in the gas sensor, and to cause such heating elements to exert their heating action in a more specific manner. Furthermore, it would be desirable to prolong the life of the electrochemical sensors, which is determined especially by the entry of moisture from the environment as a consequence of the more or less long pauses between measurements of the measuring devices. The heating of the gas sensor, especially in the area of the electrolyte, by the heater arranged on the device on the outside there, also leads to a reduction in service life due to intensified loss of water from the aqueous electrolyte.

SUMMARY AND OBJECTS OF THE INVENTION

The basic object of the present invention is to improve the ease of handling and the durability of an electrochemical gas sensor of this class without compromising the quality of measurement.

According to the invention, an electrochemical gas sensor is provided with at least two electrodes, with an electrode holder and with an electrolyte in a housing made of an electrolyte-impermeable material. The otherwise closed housing has only one inlet and outlet capillary type passage (capillaries) each for the gas to be measured. A heater, which forms a gap with the working electrode arranged above the inlet and outlet capillaries, is arranged in the housing in the flow path between the inlet and outlet capillaries.

The inlet capillaries preferably project by at least about 1 mm in relation to the surrounding inner wall of the housing. The inlet capillaries preferably have an internal diameter of at most 2 mm, and an overall length of at least about 6 mm each.

The counterelectrode and the inlet capillary are preferably arranged on the same side of the sensor, whereas the reference electrode is arranged on the opposite side with the outlet capillary. The sensor may be designed as a miniaturized component fastened directly on a corresponding evaluation board, connected via electrical contacts. The sensor may be made with platinum electrodes for breath alcohol measurement.

One essential advantage of the present invention is that, on the one hand, moisture is practically completely prevented from diffusing from the environment into the interior of the housing, especially during the rest period between measurements due to the fact that the housing is closed, except for the inlet and outlet capillaries, and, on the other hand, the action of the heater is improved, and a good interaction is ensured at the same time between the gas sample to be measured and the working electrode due to the changed routing of gas in the sensor, so that the most complete reaction of the gas component to be measured in the sample takes place, without the working electrode being partially or temporarily overloaded. The design of the subject of the present invention as a miniaturized component is especially advantageous because of the possible saving of material, the small masses to be heated, and especially because of the now possible direct arrangement of the sensor element on a corresponding evaluation board and of the possibility of integrating the sensor element on such a board. As a result, it is possible to offer a highly compact gas-measuring device which was not previously known in this design.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
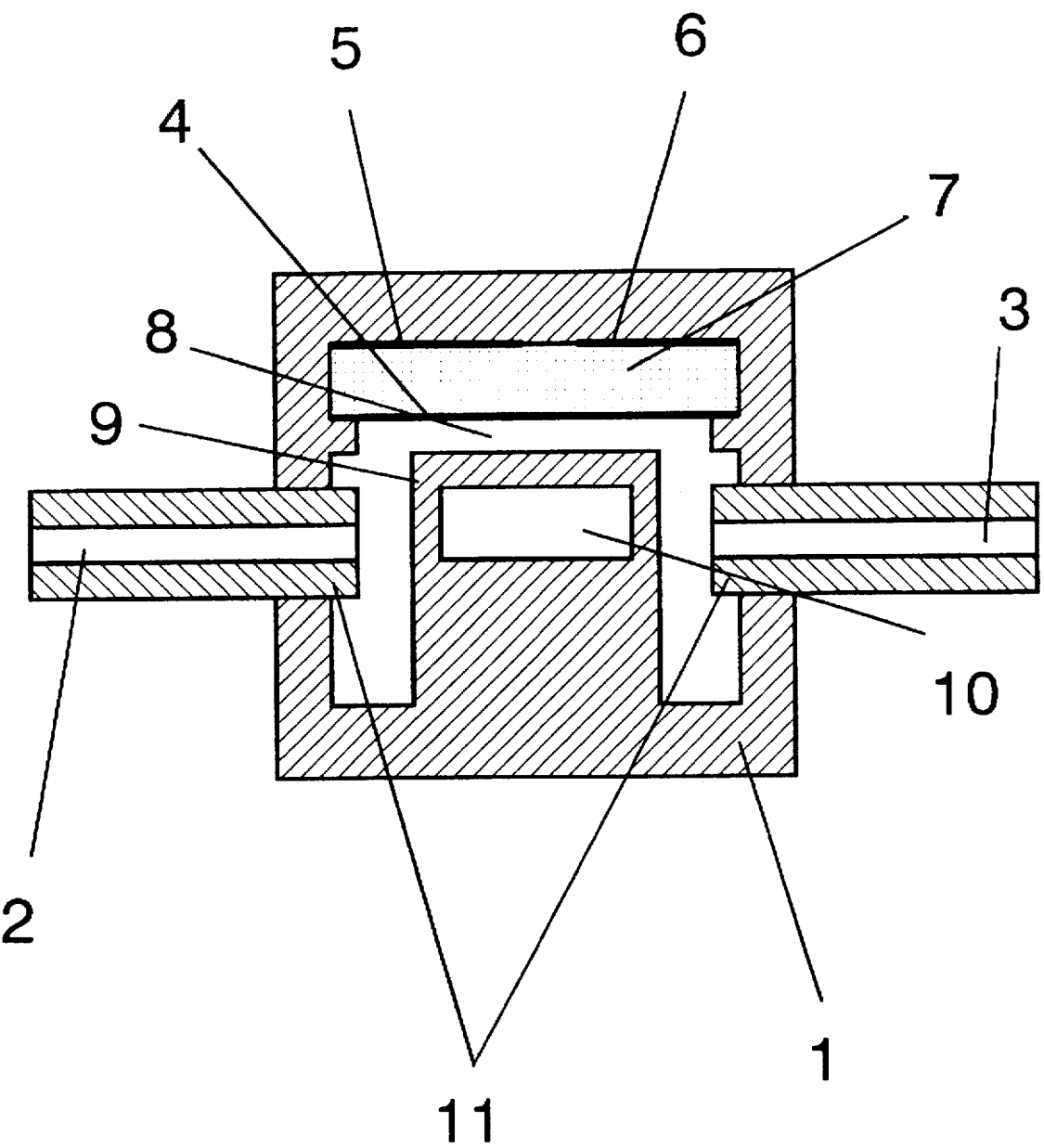
FIG. 1 is a vertical longitudinal sectional view through a gas sensor according to the present invention with a schematic representation of the most important elements.

FIG. 1 is a schematic longitudinal view of an electrochemical gas sensor according to the present invention with three electrodes in the example. The gas sensor, designed as a compact unit, is accommodated in a closed housing 1 made of an electrolyte-impermeable plastic, especially PVC, polyethylene, polypropylene, or other suitable materials. The housing 1 is preferably assembled from two one-piece partial components, e.g., an upper part and a lower part of the housing 1, which were already equipped with the other components, according to a suitable process (bonding or welding) in an electrolyte- and gas-impermeable manner. The housing 1 is accessible only through two capillaries, which are preferably also made of the same plastic as the housing 1, namely, through an inlet capillary 2 and an outlet capillary 3. In the exemplary embodiment, the electrodes, namely, one working electrode 4, one counterelectrode 5, and a reference electrode 6, are located above the inlet and outlet capillaries 2, 3. In the simplest case, the sensor has only two electrodes, i.e., the reference electrode 6 is missing.

The electrode holder 7 consists of a porous PVC matrix in the example and it is charged with a suitable electrolyte. In the case of an ethanol sensor, the electrodes consist of platinum or are coated with platinum, and acid electrolytes (sulfuric acid or phosphoric acid) are used. A heater 10 is arranged in a distributor element 9 centrally in the flow path between the inlet capillary 2 and the outlet capillary 3, and it forms a gap 8 for deflecting the gas sample to be measured to the working electrode 4 and around the heater 10. As a result, the electrolyte is not heated directly, on the one hand, and extraction of water from the electrolyte is avoided as a result, while, on the other hand, the most extensive electrochemical reaction possible of the gas component to be detected is achieved due to the two-dimensional interaction with the working electrode 4. The heater 10 is used to accelerate the special, substance-characteristic electrochemical reaction at the working electrode 4, and it leads, as a result, to a reduction in the measurement time and to a better resolution of the measurement over time. The gap 8 preferably passes over the entire width of the electrodes (at right angles to the plane of drawing). The working electrode 4 is maintained at a defined, constant potential via a potentiostat, not shown, as a result of which more rapid regeneration of the electrochemical system is achieved after exposure to the gas of a sample to be measured. The operation of the sensor with an additional reference electrode 6 and with a potentiostat, not shown, makes it also possible to operate the sensor with very small working electrodes having a surface area of less than 2 cm². Prior-art electrodes of analytical fuel cells have a surface area of about 8 cm² and therefore they do not make it possible to markedly reduce the size of the sensor while maintaining the measurement properties. The two capillaries preferably have a length of at least about 6 mm each and an internal diameter of up to 2 mm in order to minimize the diffusion of water into and out of the sensor (each capillary is preferably smaller in internal diameter than 2 mm, for example an internal diameter between 0.1 mm–1.5 mm or even between 0.2 to 0.5). It is advantageous to arrange the gas inlet through the inlet capillary 2 on the side of the sensor on which the counterelectrode 5 is also arranged, in order to avoid or minimize effects on the reference electrode 6. A projection of the inlet and outlet capillaries 2, 3 inside the sensor in relation to the inner wall of the housing 1 prevents drops of water from penetrating into the capillaries and consequently a disturbance in the path of gas from occurring. On the other hand, acid-containing drops are prevented from leaving the interior of the sensor through the outlet capillary, regardless of the position of the sensor, because these drops can be located and move only on the inner wall of the housing 1.

Figure 2:
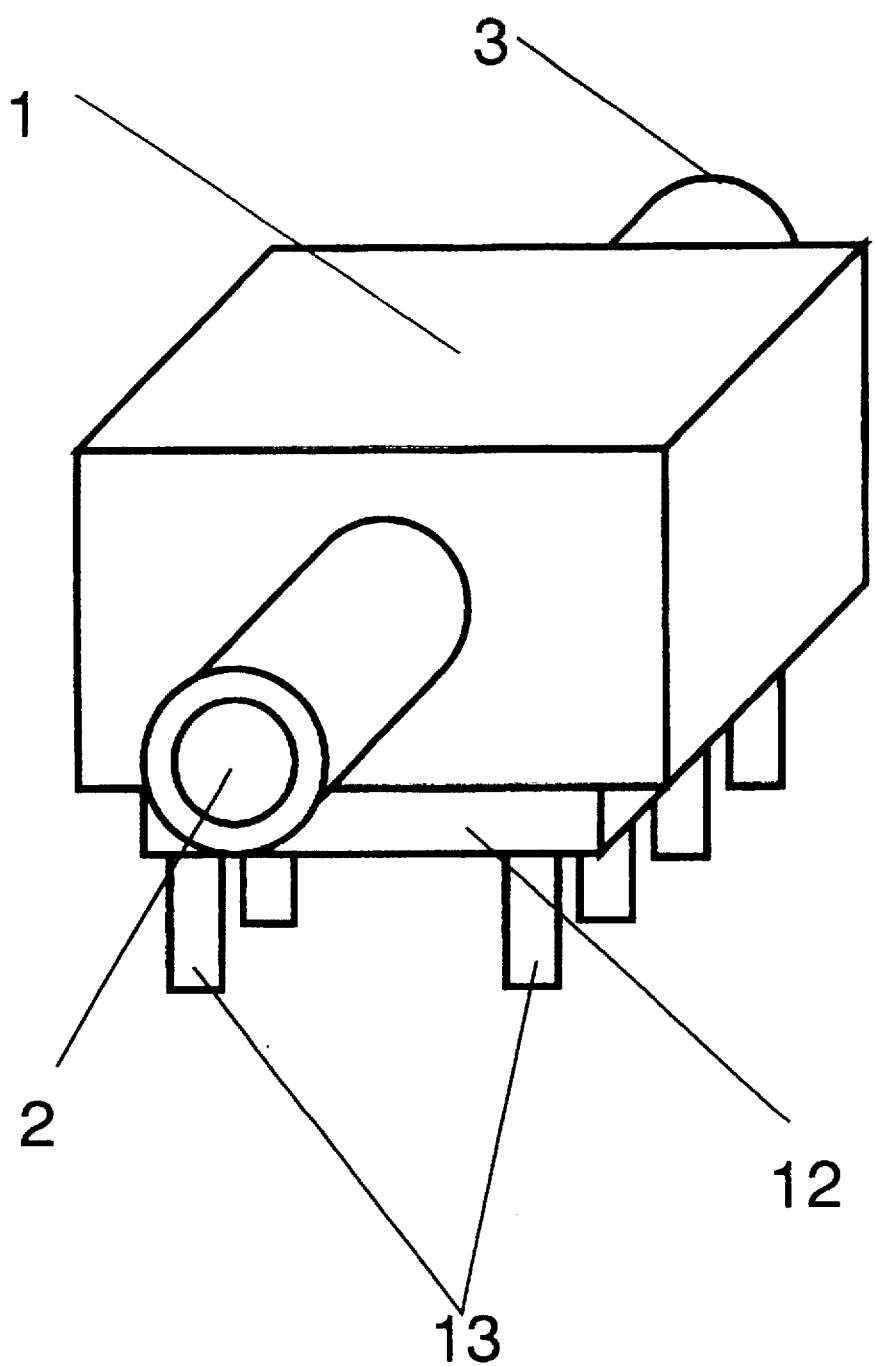
FIG. 2 is an external perspective view of a gas sensor according to the present invention in the form of a miniaturized component.

In conjunction with the distributor element 9, the gas inlet arranged in parallel to the electrodes avoids a punctiform loading of the working electrode 4. The gap 8 with a passage height of about 2 mm, which leads over the entire width of the working electrode 4, is used to cause the reacting gas component to react completely, and hindering of the throughput of gas is also markedly reduced in the case of drop formation. A heater 10, which heats the sensor, is integrated in the distributor element 9. Since the heater 10 is located inside the sensor, a relatively low heating capacity is necessary, and the heating capacity is already reduced by the miniaturization of the entire device. The location of the heater 10 opposite the electrodes causes drops of water that may have formed to evaporate in the gas space and to condense on the electrode holder 7. The small size of the sensor makes possible a plug-in connection on a standard (chip-like) base 12 (FIG. 2) and thus the direct integration on a suitable electronic evaluation unit via contacts 13. The base 12 may be connected to an integrated circuit or other similar circuit board (evaluation board) structure. The coupling with the sampling system for sampling a defined volume of gas sample to be measured is performed on the side of the outlet capillary 3 by means of a tube. Due to the length and the projection of the capillary ends, harmful contamination of the sampling mechanism is prevented from occurring in the case of drop formation in the interior of the sensor due to the drops being retained in the housing. The inlet capillary 2 extends directly into the gas flow to be measured, in the case of an alcohol sensor directly into the expired gas flow, e.g., in a suitable mouthpiece. The small amount of exchange of water into and out of the sensor leads to long service life and slight changes in its properties, which in turn makes possible longer intervals between calibrations.

While a specific embodiment of the invention has been shown and described in detail to illustrate the application of the principles of the invention, it will be understood that the invention may be embodied otherwise without departing from such principles.

What is claimed is:

1. An electrochemical gas sensor, comprising:

first and second electrodes;

an electrode holder with an electrolyte;

a housing made of an electrolyte-impermeable material, said electrode holder with said first electrode, said second electrode and said electrolyte being disposed in said housing, said housing being otherwise closed except for only one inlet and one outlet capillary passage, each capillary passage being provided for one of intake and discharge of a gas to be measured; and a heater, said heater cooperating with said first electrode to form a gap with said first electrode arranged above said inlet and outlet capillary passages in said housing in a flow path between said inlet and outlet capillary passages.

2. An electrochemical gas sensor in accordance with claim 1, wherein said inlet and outlet capillary passages project by at least about 1 mm in relation to the surrounding inner wall of the housing, have an internal diameter of at most 2 mm, and an overall length of at least about 6 mm each.

3. An electrochemical gas sensor in accordance with claim 2, wherein said second electrode is a counterelectrode, said counterelectrode and said inlet capillary being arranged on the same side of the sensor, whereas a reference electrode is arranged on an opposite side of the sensor with said outlet capillary passage.

4. An electrochemical gas sensor in accordance with claim 2, wherein said sensor is a miniaturized component fastened directly on a corresponding evaluation board and is connected to said board via electrical contacts.

5. An electrochemical gas sensor in accordance with claim 2, wherein said electrodes comprise platinum for breath alcohol measurement.

6. An electrochemical gas sensor in accordance with claim 1, wherein said second electrode is a counterelectrode, said counterelectrode and said inlet capillary being arranged on the same side of the sensor, whereas a reference electrode is arranged on an opposite side of the sensor with said outlet capillary passage.

7. An electrochemical gas sensor in accordance with claim 6, wherein said sensor is a miniaturized component fastened directly on a corresponding evaluation board and is connected to said board via electrical contacts.

8. An electrochemical gas sensor in accordance with claim 6, wherein said electrodes comprise platinum for breath alcohol measurement.

9. An electrochemical gas sensor in accordance with claim 1, wherein said sensor is a miniaturized component fastened directly on a corresponding evaluation board and is connected to said board via electrical contacts.

10. An electrochemical gas sensor in accordance with claim 1, wherein said electrodes comprise platinum for breath alcohol measurement.

11. An electrochemical gas sensor, comprising:

a housing defining an interior cavity, said housing also defining a capillary inlet passage and a capillary outlet passage, said passages communicating said interior cavity with a surrounding environment of the housing;

an electrode holder with an electrolyte;

first and second electrodes arranged on said electrode holder;

a distributor element positioned in a flow path between said inlet and outlet passages, said distributor element deflecting a gas sample from said inlet passage to said first electrode, said distributor element defining a gap with said first electrode;

a heater arranged in said distributor element.

12. An electrochemical gas sensor in accordance with claim 11, wherein:

said inlet and outlet passages are on opposite sides of said housing.

13. An electrochemical gas sensor in accordance with claim 11, wherein:

said inlet and outlet passages are aligned with each other.

14. An electrochemical gas sensor in accordance with claim 11, wherein:

said inlet and outlet passages project into said interior cavity in relation to a surrounding inner wall of said housing, each of said passages have an internal diameter of at most 2 mm, and an overall length of substantially 6 mm.

15. An electrochemical gas sensor in accordance with claim 11, wherein:

said second electrode is a counterelectrode, said counterelectrode and said inlet passage being arranged on a same side of the sensor;

a reference electrode is arranged on an opposite side of the sensor with said outlet passage, said counterelectrode and said reference electrode being on a side of said first electrode opposite said heater.

16. An electrochemical gas sensor in accordance with claim 11, wherein:

the sensor is a miniaturized component fastened directly on a corresponding evaluation board and is connected to said board via electrical contacts.

17. An electrochemical gas sensor in accordance with claim 11, wherein;

said electrodes comprise platinum for breath alcohol measurement.

\* \* \* \* \*